(12) United States Patent
Nakamura (10) Patent No.: US 8,790,292 B2
(45) Date of Patent: *Jul. 29, 2014

(54) PRESSURIZED CARBON DIOXIDE BATHING APPARATUS

(75) Inventor: Shoichi Nakamura, Higashichikuma-gun (JP)

(73) Assignees: ACP Japan Co., Ltd., Tokyo (JP); Shoichi Nakamura, Higashichikuma-gun, Nagano (JP)

( * ) Notice: Subject to any disclaimer, the term of this patent is extended or adjusted under 35 U.S.C. 154(b) by 367 days.

This patent is subject to a terminal disclaimer.

(21) Appl. No.: 12/452,529

(22) PCT Filed: Feb. 8, 2008

(86) PCT No.: PCT/JP2008/052178
§ 371 (c)(1), (2), (4) Date: Feb. 23, 2010

(87) PCT Pub. No.: WO2009/008187
PCT Pub. Date: Jan. 15, 2009

(65) Prior Publication Data
US 2010/0168650 A1   Jul. 1, 2010

(30) Foreign Application Priority Data
Jul. 9, 2007   (JP) .................................. 2007-179368

(51) Int. Cl.
*A61M 37/00*   (2006.01)
*A61M 35/00*   (2006.01)
*A61H 9/00*   (2006.01)
*A61H 33/14*   (2006.01)

(52) U.S. Cl.
CPC ........ *A61H 9/0078* (2013.01); *A61H 2033/145* (2013.01); *A61H 2205/08* (2013.01); *A61H 2205/10* (2013.01); *A61M 35/00* (2013.01); *A61H 33/14* (2013.01)
USPC .......................................................... 604/24

(58) Field of Classification Search
CPC .................... A61H 2033/145; A61H 2205/08; A61H 2205/10; A61H 33/14; A61H 9/0078; A61M 35/00
USPC ................ 604/24; 607/80, 81, 83, 84, 86, 91; 4/535
See application file for complete search history.

(56) References Cited

U.S. PATENT DOCUMENTS

| 5,810,795 A * | 9/1998 | Westwood ..................... 604/305 |
| 6,572,594 B2 * | 6/2003 | Satterfield et al. ............. 604/290 |
| 6,638,270 B2 * | 10/2003 | Johnson ..................... 604/890.1 |
| 2006/0185670 A1 * | 8/2006 | Loori et al. ............... 128/202.12 |
| 2009/0255531 A1 * | 10/2009 | Johnson et al. ............... 128/99.1 |

FOREIGN PATENT DOCUMENTS

| JP | H04-343849 | 11/1992 | |
| JP | 07171189 A * | 7/1995 | ............. A61H 33/14 |
| JP | 2005-058745 | 3/2005 | |

(Continued)

*Primary Examiner* — Emily Schmidt
*Assistant Examiner* — Michael J Anderson
(74) *Attorney, Agent, or Firm* — Manabu Kanesaka (57) ABSTRACT

Provided is a pressurized carbon dioxide bathing apparatus for bringing carbon dioxide into contact with skin of a living body by a predetermined pressure value or more using compressed air, and thereby enabling carbon dioxide to be absorbed efficiently from the skin, and the pressurized carbon dioxide bathing apparatus is comprised of a carbon dioxide supply means 1 for supplying a mixed gas of carbon dioxide and water vapor containing one or a plurality of chemical agents, a compressed air supply means 2, and a cover suit 3 of a two-layer structure having an enclosed layer 4 that is connected to the carbon dioxide supply means 1 via a connector 6 to confine the mixed gas supplied from the carbon dioxide supply means 1 so as to bring the mixed gas into direct contact with skin of the human body and an enclosed layer 5 that is connected to the compressed air supply means 2 via a connector 7 to confine compressed air supplied from the compressed air supply means 2, where the carbon dioxide is brought into contact with skin of the human body with a predetermined pressure value or more by the compressed air.

19 Claims, 8 Drawing Sheets

(56) References Cited

FOREIGN PATENT DOCUMENTS

| | | |
|---|---|---|
| JP | 2005-168859 | 6/2005 |
| JP | 2006-020985 | 1/2006 |
| JP | 2006-263253 | 10/2006 |
| JP | 2007-159902 | 6/2007 |
| JP | 2007-181720 | 7/2007 |

* cited by examiner

PRESSURIZED CARBON DIOXIDE BATHING APPARATUS

TECHNICAL FIELD

The present invention relates to a pressurized carbon dioxide bathing apparatus for bringing carbon dioxide into direct contact with skin of a living body, thereby enlarging the blood vessel and improving the blood circulation, and more particularly, to a pressurized carbon dioxide bathing apparatus for bringing carbon dioxide into contact with skin of a living body by a predetermined pressure value or more using compressed air, and thereby enhancing absorption efficiency of carbon dioxide from the skin.

BACKGROUND ART

Conventionally, it has been known that the blood vessel is enlarged when carbon dioxide ($CO_2$) is absorbed from skin of a living body. Carbon dioxide penetrates skin by simply contacting the skin, enlarges the blood vessel of the penetration site, improves the blood circulation, and therefore, exerts various physiological effects of reducing the blood pressure, easing loads on the heart, improving metabolism, promoting the elimination of pain substances and waste products, etc.

Therefore, carbonated spring bathing and the like have been used for treatments for high blood pressure, heart disease and arteriosclerosis or the like. Further, recently, as well as the medical purpose, carbon dioxide has received attention in terms of health enhancement and cosmetic promotion by the blood circulation promoting effect.

As an example of conventional techniques to cause carbon dioxide to be absorbed into the human body, used the most widely are bath agents that generate carbon dioxide by being immersed in hot water in a bath. When a bath agent is put into hot water, carbon dioxide trapped in the bath agent appears in hot water in bubble form, part of carbon dioxide is dissolved in the hot water and contacts skin of a bathing person, and it is thus intend to osmose carbon dioxide from the skin into the body so as to exert the physiological effects as described above.

Further, as the conventional technique for bringing a larger amount of carbon dioxide into contact with the human body, carbon oxide bathing apparatuses are known (for example, Patent Documents 1, 2 and 3).

This kind of apparatus is to dissolve carbon dioxide in water in high concentrations, and Patent Document 1 discloses a bath-agent carbon-dioxide dispersing apparatus comprised of a carbon-dioxide bath-agent dissolving portion 2 and a carbon dioxide dispersing apparatus 1 having micropores 4, where bubbles of carbon dioxide become minute by both of micropores 3 provided between the dissolving portion 2 and the dispersing apparatus 1 and the micropores 4 provided in the dispersing apparatus portion, the area such that carbon dioxide contacts water in the bath significantly increases while the contact time is increased, and the bath agent is further prevented from floating due to bubbles around the bath agent, and thus, is intended to continue dissipating carbon oxide inside water in the bath until the end.

Further, in Patent Documents 2 and 3 are described a bath microbubble generating apparatus and carbon dioxide combined shower bathing apparatus where a bath is connected to a carbon dioxide generating apparatus, and a large amount of carbon dioxide supplied from the carbon dioxide generating apparatus is jetted in fine-bubble form to be actively dissolved in bath water in the bath.

Patent Document 1: Japanese Laid-Open Patent Publication No. 2006-20985
Patent Document 2: Japanese Laid-Open Patent Publication No. 2007-159902
Patent Document 3: Japanese Laid-Open Patent Publication No. 2005-168859

DISCLOSURE OF INVENTION

Problems to be Solved by the Invention

However, the conventional techniques of above-mentioned Patent Documents 1 to 3 are to dissolve carbon dioxide in water in a bath in bathing to be absorbed from skin of the human body, and have problems that the absorptance of carbon dioxide from skin is not high although a large amount of carbon dioxide is consumed. Further, the use is limited to the time of bathing.

The present invention was made in view of the above-mentioned conventional problems, and it is an object of the invention to provide a pressurized carbon dioxide bathing apparatus for enabling even a small amount of carbon dioxide to be efficiently absorbed from skin of a living body.

Means for Solving the Problem

Therefore, the present invention provides a pressurized carbon dioxide bathing apparatus which is to bring carbon dioxide with a concentration of a predetermined value or more into contact with skin of the human body, thereby enlarge the blood vessel and improve the blood circulation, and which is characterized by being comprised of a carbon dioxide supply means for supplying carbon dioxide being contained in water vapor containing one or a plurality of chemical agents, a compressed air supply means, and a cover suit of a two-layer structure which is connected to the carbon dioxide supply means and the compressed air supply means via connectors, and brings a mixed gas of carbon dioxide and water vapor containing one or a plurality of chemical agents supplied from the carbon dioxide supply means into direct contact with skin of the human body, while forming an enclosed layer for confining the compressed air supplied from the compressed air supply means, where the carbon dioxide is brought into contact with skin of the human body with a predetermined pressure value or more by the compressed air.

Further, the invention provides a pressurized carbon dioxide bathing apparatus which is to bring carbon dioxide with a concentration of a predetermined value or more into contact with skin of an animal, thereby enlarge the blood vessel and improve the blood circulation, and which is characterized by being comprised of a carbon dioxide supply means for supplying carbon dioxide being contained in water vapor containing one or a plurality of chemical agents, a compressed air supply means, and a cover suit of a two-layer structure which is connected to the carbon dioxide supply means and the compressed air supply means via connectors, and brings a mixed gas of carbon dioxide and water vapor containing one or a plurality of chemical agents supplied from the carbon dioxide supply means into direct contact with skin of the animal, while forming an enclosed layer for confining the compressed air supplied from the compressed air supply means, where the carbon dioxide is brought into contact with skin of the animal with a predetermined pressure value or more by the compressed air.

Thus, in the pressurized carbon dioxide bathing apparatus, the compressed air layer formed in the cover suit presses, by a certain pressure, the mixed gas of carbon dioxide and water vapor containing one or a plurality of chemical agents directly contacting skin of the human body or an animal, and thereby remarkably enhances permeability of carbon dioxide from the skin. Further, since it is not necessary to increase the pressure of the mixed gas itself, a large amount of carbon dioxide is not required, and it is possible to efficiently use carbon dioxide.

Further, the pressurized carbon dioxide bathing apparatus of the invention is applicable to not only the human body, but also animals (for example, racehorses, pets, etc.).

Herein, the compressed air supply means may always perform pressurization using the compressed air, but may perform interval pressurization for repeating pressurization and depressurization on the compressed air at predetermined time intervals. It is naturally possible to enhance permeability of carbon dioxide from skin by continuous pressurization, and it is possible to further improve permeability by pressurizing at intervals.

Herein, the carbon dioxide supply apparatus used in the pressurized carbon dioxide bathing apparatus is provided with a carbon dioxide inserting portion in which is inserted a carbon dioxide bottle with carbon dioxide filled therein, and a water-retaining portion for receiving the water containing one or a plurality of chemical agents, releases the carbon dioxide inside the carbon oxide bottle into the water-retaining portion in bubble form of fine-particle size, and thereby obtains the mixed gas of carbon dioxide and water vapor containing one or a plurality of chemical agents.

At this point, the one or a plurality of chemical agents is either one or some of vitamin E, vitamin C, photocatalyst and apatite and a complex of cyclodextrin. By this means, it is possible to further add effects such as blood circulation promotion, sterilization and the like specific to each chemical agent.

Then, the temperature of water inside the carbon dioxide supply apparatus is set at the range of 40° to 70° C., and it is thereby made possible to warm skin as in bathing to enable the blood circulation to be excellent by itself.

Further, the compressed air supply means is provided with a heating means, and is capable of supplying hot air or cool air by ON/OFF of the heating means.

Then, the air pressure supplied from the compressed air supply means is set at the range of 1.2 to 2.5 atmospheres. By this means, it is possible to further produce the pressure-massage effect on skin by the compressed air.

Therefore, the compressed air supply means uses (1) compressed air bottle, (2) electrically driven compressor, or (3) manual bag-shaped air pressure device (for example, manual air bag used in a blood pressure gauge or foot-operated type air pressure device for filling air in a float).

Herein, as the cover suit, various cover suits can be used such as, for example, a cover suit for the lower body to envelop the lumbar part and lower limbs of the human body, cover suit for the upper body to envelop the abdominal part and upper limbs of the human body, cover suit for the single lower limb to envelop one leg of the human body, and cover suit for the single upper limb to envelop one hand of the human body. Then, some of these various kinds of cover suits can be used concurrently.

Then, the cover suit is formed from any one or a combination of some of polyethylene, polypropylene, polyvinylidene chloride, polystyrene, polyvinyl acetate, polyvinyl chloride, nylon or polytetrafluoroethylene and woven fabric or nonwoven fabric. Further, the cover suit is provided at its opening portion with a fastening means that is a cord or hook-and-loop fastener, and thereby prevents the mixed gas of carbon dioxide and water vapor and the compressed air from dissipating into the atmosphere.

Each of the connectors, which are provided in the cover suit to receive the mixed gas from the carbon dioxide supply means and the compressed air from the compressed air supply means, is a screw-type connector or an insert-type connector with a tap formed therein.

Advantageous Effect of the Invention

The pressurized carbon dioxide bathing apparatus according to the invention has a cover suit of a two-layer structure which has an enclosed layer for confining a mixed gas of carbon dioxide and water vapor supplied from the carbon dioxide supply means to bring the mixed gas of carbon dioxide and water vapor into direct contact with skin of a living body, while having an enclosed layer for confining compressed air supplied from the compressed air supply means, thereby brings carbon dioxide into contact with skin of the living body by a predetermined pressure value or more using the compressed air, and thus remarkably enhances permeability of carbon dioxide from the skin. Further, since it is not necessary to increase the pressure of the mixed gas of carbon dioxide and water vapor itself, a large amount of carbon dioxide is not required, and it is possible to cause carbon dioxide to be efficiently absorbed from the skin. Furthermore, since carbon dioxide is supplied while being contained in water vapor containing one or a plurality of chemical agents, it is possible to further add effects such as blood circulation promotion, sterilization and the like specific to each chemical agent.

DESCRIPTION OF SYMBOLS

1 Carbon dioxide supply apparatus
2 Compressor
3, 30, 40, 50, 60, 70 Cover suit
3A, 30A, 40A, 50A, 60A, 70A Inner cover suit 3B, 30B, 40B, 50B, 60B, 70B Outer cover suit
4, 31, 41, 51, 61, 71 Mixed gas layer of carbon dioxide and water vapor
5, 32, 42, 52, 62, 72 Pressurizing layer
6, 7 Hose
6a, 7a Connector
8, 33, 34, 43, 53, 63, 73 Fastening portion
9 Skin
12 Warm water filling opening
13 Water-retaining tank
14 Carbon dioxide inserting portion
15 Mixed gas supply opening
16 Cap
17 Carbon dioxide bottle
18 Carbon dioxide
19 Warm water
20 Mixed gas of carbon dioxide and water vapor
54 Air supply bulb
64 Frame

BEST MODE FOR CARRYING OUT THE INVENTION

Embodiments of the invention will specifically be described below with reference to drawings.

Embodiment 1

Figure 1:
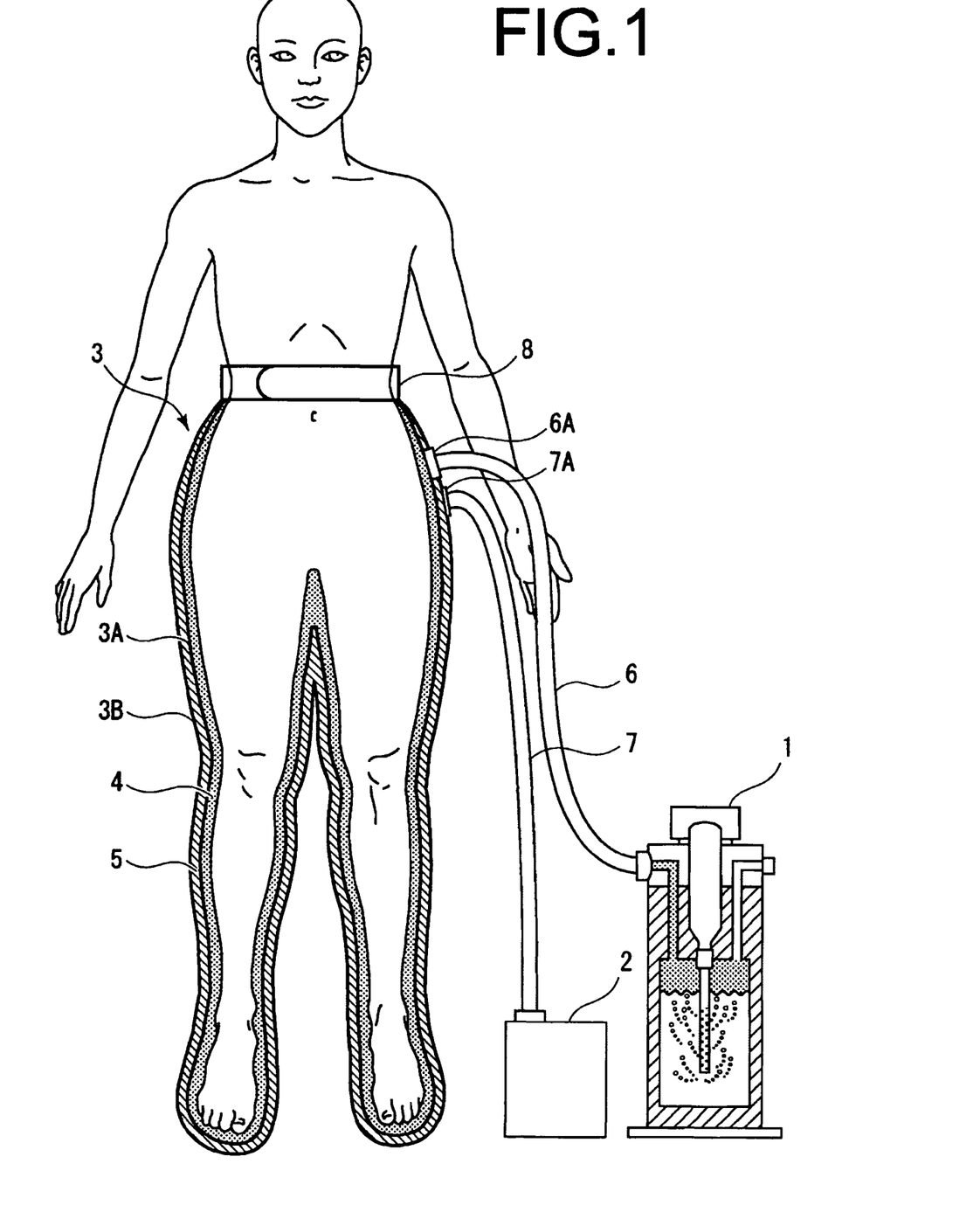
FIG. 1 is an entire schematic view of a pressurized carbon dioxide bathing apparatus (for the lower body) according to Embodiment 1 of the invention.
Figure 2:
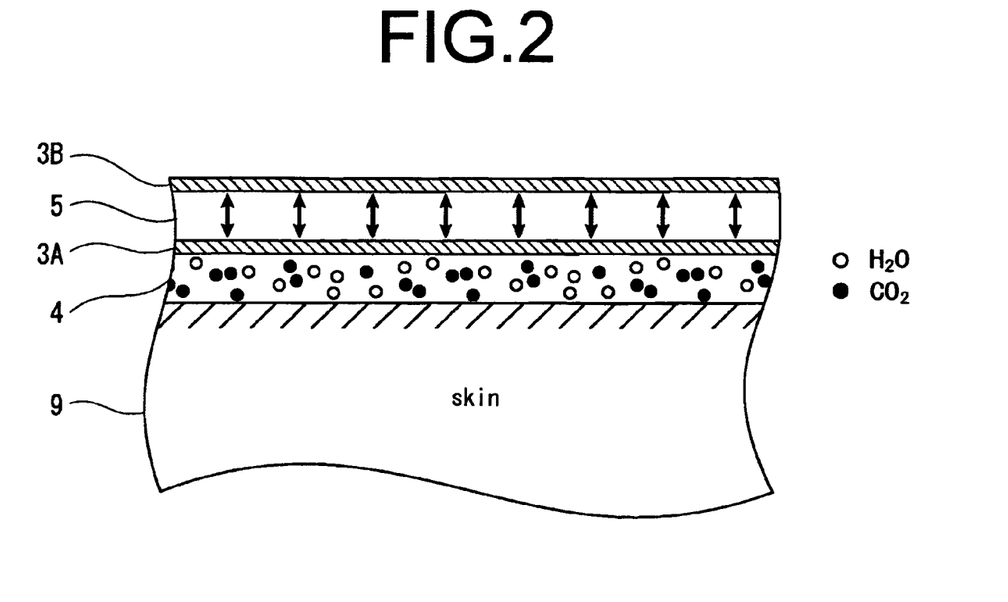
FIG. 2 is a principal-part enlarged view showing the contact relationship between the cross section of the cover suit and skin in the pressurized carbon dioxide bathing apparatus according to Embodiment 1 of the invention.
Figure 3:
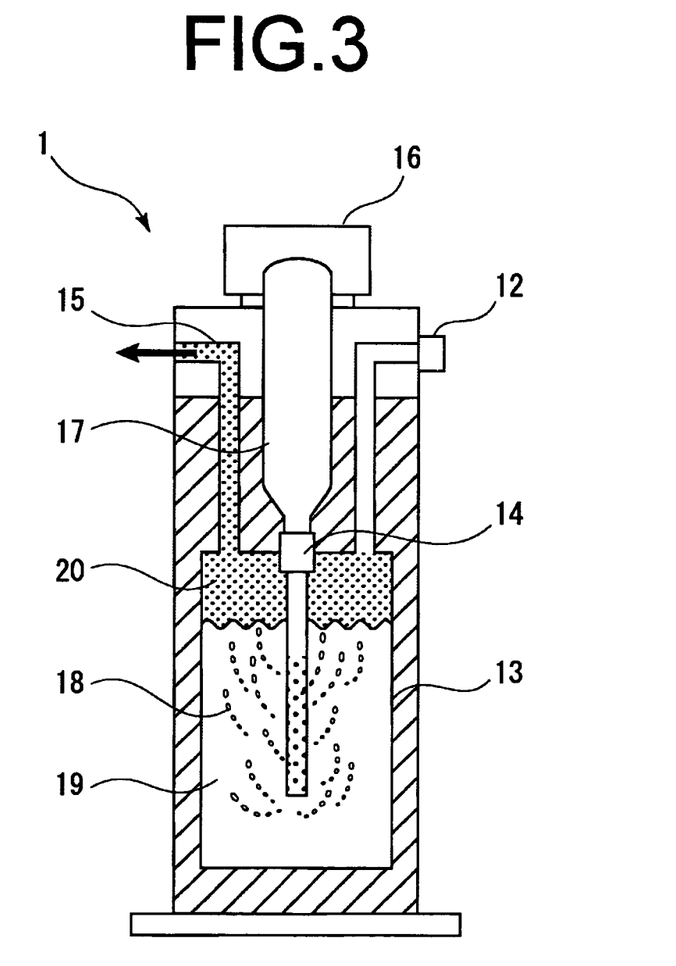
FIG. 3 is a schematic view of a carbon dioxide supply apparatus of the pressurized carbon dioxide bathing apparatus according to Embodiment 1 of the invention.

FIG. 1 is an entire schematic view of a pressurized carbon dioxide bathing apparatus (for the lower body) according to Embodiment 1 of the invention. Further, FIG. 2 is a principal-part enlarged view showing the contact relationship between the cross section of the cover suit and skin, and FIG. 3 is a schematic view of a carbon dioxide supply apparatus.

As shown in FIG. 1, the pressurized carbon dioxide bathing apparatus according to this Embodiment is comprised of a carbon dioxide supply apparatus 1 for supplying carbon dioxide being contained in water vapor, a compressor 2 for supplying compressed air, a cover suit 3 with integrally formed inner cover suit 3A that covers the human body (herein, the lower body as an example) and that is filled with the mixed gas of carbon dioxide and water vapor to cause the mixed gas to contact skin of this area to be absorbed, and outer cover suit 3B that is filled with compressed air to pressurize the mixed gas inside the inner cover suit 3A, a hose 6 as a connector that connects between the carbon dioxide supply apparatus 1 and inner cover suit 3A to supply the mixed gas of carbon dioxide and water vapor into the inner cover suit 3A, and a hose 7 as a connector that connects between the compressor 2 and outer cover suit 3B to supply compressed air into the outer cover suit 3B.

As described above, the cover suit 3 has the shape of covering and enveloping the human body (herein, lower body), where two layers of the inner cover suit 3A and outer cover suit 3B are integrally formed. The cover suit 3 is provided at its opening portion to put on/off with a fastening portion 8 to prevent the mixed gas of carbon dioxide and water vapor from leaking. The inside of the cover suit 3 is sealed by the fastening portion 8, and to the inside of the inner cover suit 3A is supplied the mixed gas of carbon dioxide and water vapor from the carbon dioxide supply apparatus 1, while to the inside of the outer cover suit 3B is supplied compressed air from the compressor 2, via the hoses 6 and 7, respectively. By this means, as shown in FIG. 2, a mixed gas layer 4 of carbon dioxide and water vapor is formed between the inner cover suit 3A and skin 9, and a pressurizing layer 5 comprised of compressed air is formed between the inner cover suit 3A and outer cover suit 3B. The pressurizing layer 5 pressurizes the mixed gas layer 4 of carbon dioxide and water vapor against skin 9 from the outside to promote absorption of carbon dioxide from skin 9.

The fastening portion 8 provided in the cover suit 3 is comprised of a stretch material fitting the body, and for example, by hook-and-loop fasteners, is fastened at a position in accordance with the body shape of a user to seal the inside of the cover suit 3. In addition, since the inner cover suit 3A and outer cover suit 3B are woven into the fastening portion 8, the pressurizing layer 5 beforehand has a structure with hermeticity. Herein, as the fastening means in the fastening portion 8, a cord, rubber band or combination thereof may be used, as well as the hook-and-loop fastener. Further, such a structure may be adopted that enables fastening by tightening with air pressure.

The cover suit 3 is formed of a non-breathable material (for example, any one or a combination of some of polyethylene, polypropylene, polyvinylidene chloride, polystyrene, polyvinyl acetate, polyvinyl chloride, nylon, polytetrafluoroethylene, woven fabric and non-woven fabric, etc.).

In addition, as shown in FIG. 1, the inner cover suit 3A is provided with a connector 6A to connect the other end of the hose 6 with one end thereof connected to the carbon dioxide supply apparatus 1. Meanwhile, also the outer cover suit 3B is provided with a connector 7A to connect the other end of the hose 7 with one end thereof connected to the compressor 2. In addition, the hoses 6, 7 are provided at their end portions with taps, and can be connected to the connectors 6A, 7A in a screw type or insert type, respectively. Further, the hoses are provided at their inside with non-return valves to prevent back flow of the gas.

As shown in FIG. 3, the carbon dioxide supply apparatus 1 is an apparatus to obtain a mixed gas of carbon dioxide and water vapor by releasing carbon dioxide into warm water. The carbon dioxide supply apparatus 1 is comprised of a warm water filling opening 12 for filling warm water 19, a water-retaining tank 13 for retaining the warm water 19 filled from the warm water filling opening 12, a carbon dioxide inserting portion provided at its inside with a needle to open a carbon dioxide bottle 17 to release carbon dioxide 18 into the warm water 19 inside the water-retaining tank 13, a mixed gas supply opening 15 for retrieving a mixed gas 20 of carbon dioxide and water vapor generated by releasing the carbon dioxide 18 into the warm water 19, and a cap 16 to secure the carbon dioxide bottle 17, while pressing the carbon dioxide bottle 17 against the carbon dioxide inserting portion 14.

Then, first, the warm water 19 with temperatures ranging from about 40° to 70° C. is filled into the water-retaining tank 13 from the warm water filling opening 12. Next, the carbon dioxide bottle 17 is inserted in the carbon dioxide inserting portion 14. By screwing the cap 16, the carbon dioxide bottle 17 is pressed down, and when the cap 16 is screwed completely, the carbon dioxide bottle 17 is opened by the needle provided inside the carbon dioxide inserting portion 14. Then, the carbon dioxide 18 is swiftly released into the warm water 19. By this means, the mixed gas 20 of the carbon dioxide and water vapor is produced, and supplied to the inside of the inner cover suit 3A from the mixed gas supply opening 15 through the hose 6.

Herein, as described above, carbon dioxide has physiological effects of penetrating from skin, enlarging the blood vessel and promoting the blood circulation. Further, in the pressurized carbon dioxide bathing apparatus, by adding a chemical agent such as menthol causing the relief effect, vitamin E to further promote the blood circulation, vitamin C to make the skin beautiful, chemical agent (for example, complex of photocatalyst and apatite) to decontaminate bacteria, etc adhered to the surface of skin to sterilize, and/or cyclodextrin, etc. to enhance the pharmacological effects of these chemical agents and the like to the warm water 19 to fill into the water-retaining tank 13 from the warm water filling opening 12, it is also possible to produce synergistic physiological effects with the physiological effects by carbon dioxide.

In addition, the configuration of the carbon dioxide supply apparatus 1 is not limited to that as described above. For example, the cartridge-type small-size carbon dioxide bottle 17 is used herein as an example, but as a substitute for the bottle 17, the apparatus 1 may be connected to an industrial large-size gas bottle, etc. via a valve.

The compressor 2 supplies compressed air to the pressurizing layer 5 of the cover suit 3. At this point, the air pressure of supplied compressed air is set at the range of about 1.2 to 2.5 atmospheres. In addition, pressurization by compressed air from the compressor 2 may be always performed, and the effects can further be enhanced by pressurizing at intervals. The interval pressurization may be repetition of pressurization and depressurization at intervals ranging from several seconds to several dozen seconds.

As the compressor 2, a compressed air bottle is preferably used. As well as the compressed air bottle, to use the apparatus 1 readily at home, for example, a household futon dryer or the like may be used. Further, the compressor 2 preferably supplies hot air or cold air using a heater.

In addition, only the lower body is targeted in the above-mentioned Embodiment, and varying the shape of the cover suit enables pressurized carbon dioxide bathing to be performed on various body parts.

Embodiment 2

Figure 4:
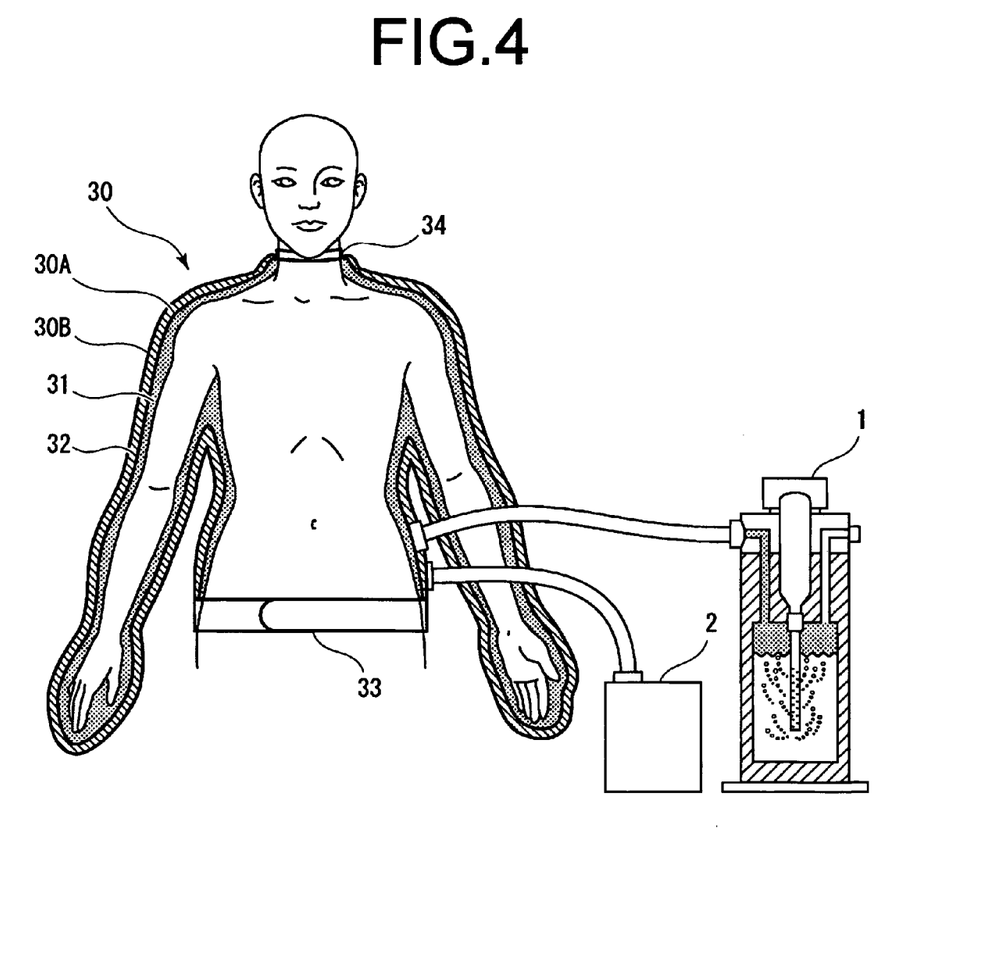
FIG. 4 is a schematic view of a pressurized carbon dioxide bathing apparatus (for the upper body) according to Embodiment 2 of the invention.

FIG. 4 is a schematic view of a pressurized carbon dioxide bathing apparatus (for the upper body) according to Embodiment 2 of the invention.

Described herein is a pressurized carbon dioxide bathing apparatus for the purpose of performing pressurized carbon dioxide bathing on the upper body. In addition, in FIG. 4, parts with the same configurations as in FIG. 1 are assigned the same reference numerals to omit descriptions thereof.

In FIG. 4, a cover suit 30 is formed from an inner cover suit 30A and outer cover suit 30B. The inner cover suit 30A and outer cover suit 30B are formed integrally, to the inside of the inner cover suit 30A is supplied the mixed gas of carbon dioxide and water vapor from the carbon dioxide supply apparatus 1, and to the inside of the outer cover suit 30B is supplied compressed air from the compressor 2. By this means, a mixed gas layer 31 of carbon dioxide and water vapor is formed between the inner cover suit 30A and skin, and a pressurizing layer 32 comprised of compressed air is formed between the inner cover suit 30A and outer cover suit 30B. The pressurizing layer 32 pressurizes the mixed gas layer 31 of carbon dioxide and water vapor against the skin from the outside to promote absorption of carbon dioxide from the skin.

As shown in FIG. 4, in this Embodiment, the cover suit 30 has the shape of covering and enveloping the entire upper body. In an opening of the lumbar part, a fastening portion 33 is provided, fastened to fit the body at a position in accordance with the body shape of a user, and prevents the gas from leaking. In addition, also in an opening of the neck part, a fastening portion 34 is provided to facilitate putting on/off, while preventing the gas from leaking. Each of the fastening portions 33 and 34 is preferably formed of a cord, rubber band or combination thereof, as well as the hook-and-loop fastener. Further, such a structure may be adopted that enables fastening by tightening with air pressure.

Embodiment 3

Figure 5:
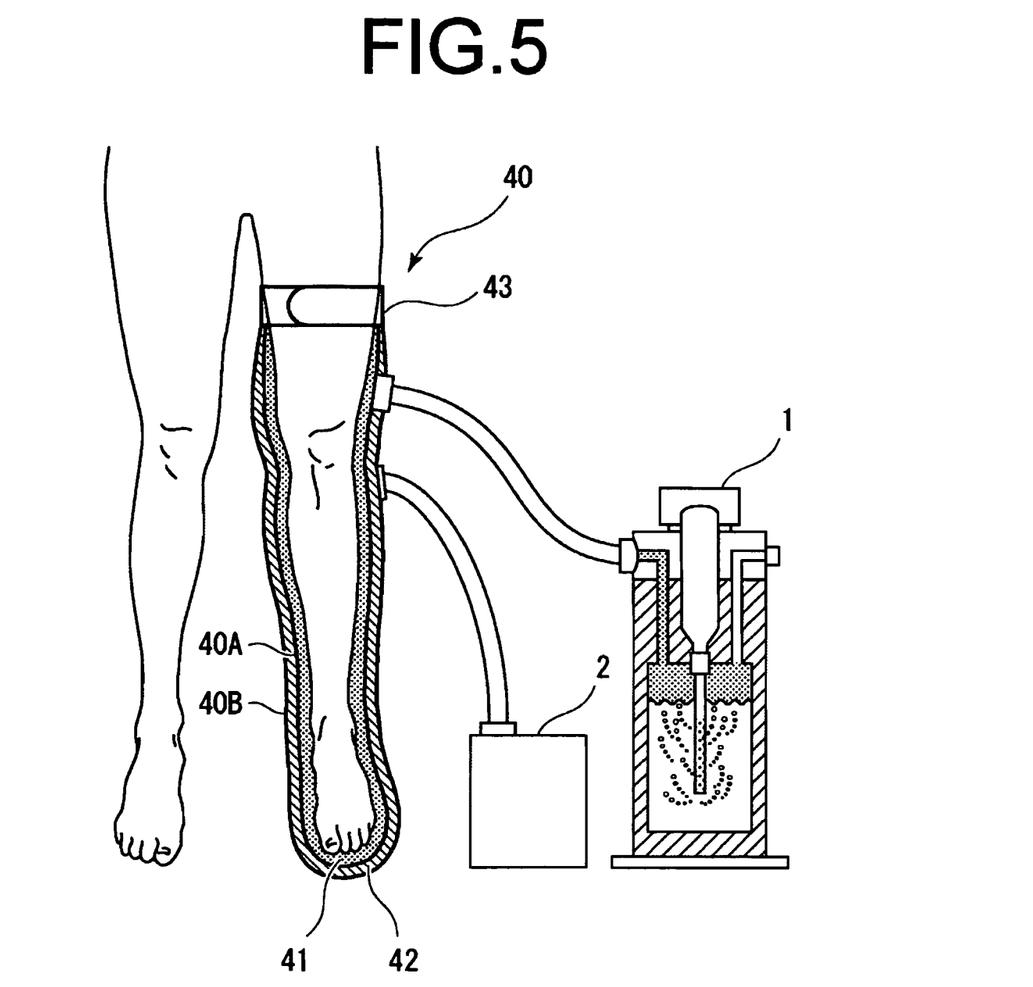
FIG. 5 is a schematic view of a pressurized carbon dioxide bathing apparatus (for the single lower limb) according to Embodiment 3 of the invention.

FIG. 6 is a schematic view of a pressurized carbon dioxide bathing apparatus (for the single lower limb) according to Embodiment 3 of the invention.

Described herein is a pressurized carbon dioxide bathing apparatus for the purpose of performing pressurized carbon dioxide bathing on the single lower limb. In addition, in FIG. 5, parts with the same configurations as in FIG. 1 are assigned the same reference numerals to omit descriptions thereof.

In FIG. 5, a cover suit 40 is formed from an inner cover suit 40A and outer cover suit 40B. The inner cover suit 40A and outer cover suit 40B are formed integrally, to the inside of the inner cover suit 40A is supplied the mixed gas of carbon dioxide and water vapor from the carbon dioxide supply apparatus 1, and next, to the inside of the outer cover suit 40B is supplied compressed air from the compressor 2. By this means, a mixed gas layer 41 of carbon dioxide and water vapor is formed between the inner cover suit 40A and skin, and a pressurizing layer 42 comprised of compressed air is formed between the inner cover suit 40A and outer cover suit 40B. The pressurizing layer 42 pressurizes the mixed gas layer 41 of carbon dioxide and water vapor against the skin from the outside to promote absorption of carbon dioxide from the skin.

As shown in FIG. 5, in this Embodiment, the cover suit 40 has the shape of covering and enveloping the single lower limb. In an opening of the femoral region, a fastening portion 43 is provided, fastened to fit the body at a position in accordance with the body shape of a user, and prevents the gas from leaking. The fastening portion 43 is preferably formed of a cord, rubber band or combination thereof, as well as the hook-and-loop fastener. Further, such a structure may be adopted that enables fastening by tightening with air pressure.

Embodiment 4

Figure 6:
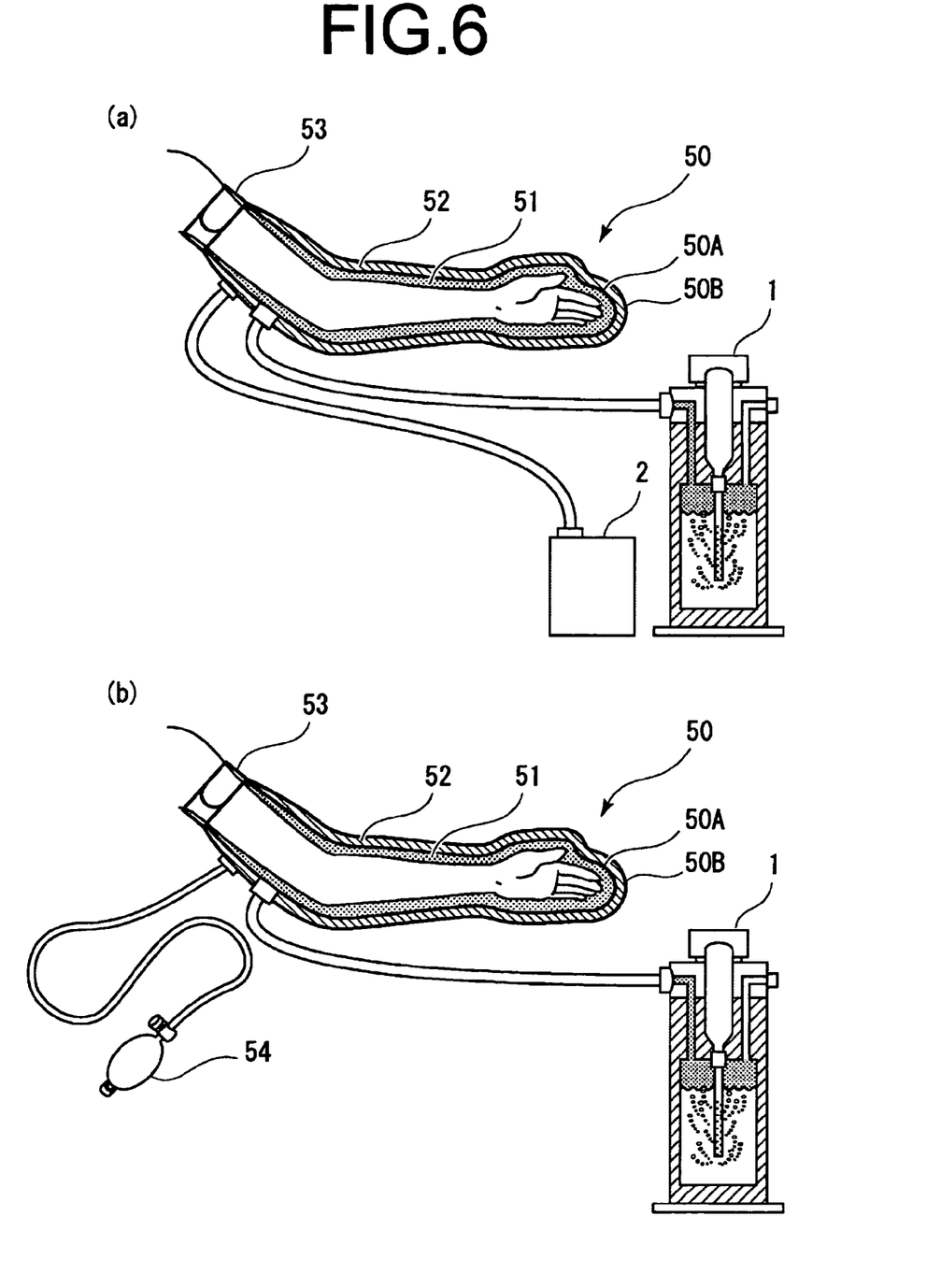
FIG. 6 contains schematic views of pressurized carbon dioxide bathing apparatuses (for the single upper limb) according to Embodiment 4 of the invention.

FIG. 6 is a schematic view of a pressurized carbon dioxide bathing apparatus (for the single upper limb) according to Embodiment 4 of the invention.

Described herein is a pressurized carbon dioxide bathing apparatus for the purpose of performing pressurized carbon dioxide bathing on the single upper limb. In addition, in FIG. 6, parts with the same configurations as in FIG. 1 are assigned the same reference numerals to omit descriptions thereof.

In FIG. 6, a cover suit 50 is formed from an inner cover suit 50A and outer cover suit 50B. The inner cover suit 50A and outer cover suit 50B are formed integrally, to the inside of the inner cover suit 50A is supplied the mixed gas of carbon dioxide and water vapor from the carbon dioxide supply apparatus 1, and next, to the inside of the outer cover suit 50B is supplied compressed air from the compressor 2. By this means, a mixed gas layer 51 of carbon dioxide and water vapor is formed between the inner cover suit 50A and skin, and a pressurizing layer 52 comprised of compressed air is formed between the inner cover suit 50A and outer cover suit 50B. The pressurizing layer 52 pressurizes the mixed gas layer 51 of carbon dioxide and water vapor against the skin from the outside to promote absorption of carbon dioxide from the skin.

As shown in FIG. 6, in this Embodiment, the cover suit 50 has the shape of covering and enveloping the single upper limb. In an opening of the upper arm region, a fastening portion 53 is provided, fastened to fit the body at a position in accordance with the body shape of a user, and prevents the gas from leaking. The fastening portion 53 is preferably formed of a cord, rubber band or combination thereof, as well as the hook-and-loop fastener. Further, such a structure may be adopted that enables fastening by tightening with air pressure.

In addition, in FIG. 6(a), the compressor 2 is disposed as in the other Embodiments as a compressed air supply means, and in FIG. 6(b), as a substitute for the compressor 2, a bag-shaped air supply bulb 54 is disposed as a manual air pressure device. For example, the air supply bulb 54 has the same configuration as that of a pressurizing air supply bulb of a manual blood pressure gauge, is made of rubber or the like, supplies air into the pressurizing layer 52 by hand, and thereby enables pressurization to be performed easily.

Embodiment 5

Figure 7:
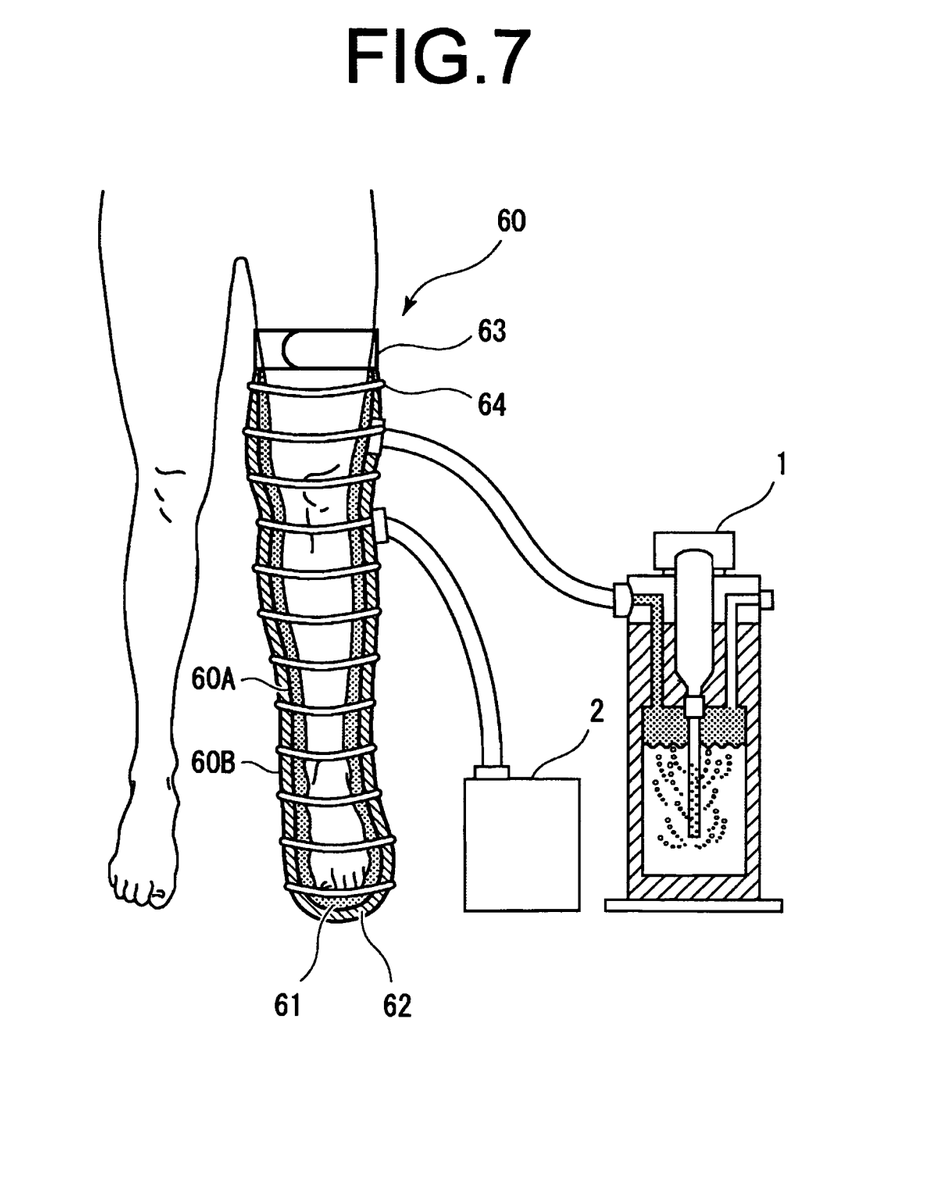
FIG. 7 is a schematic view of a pressurized carbon dioxide bathing apparatus (with a frame) according to Embodiment 5 of the invention.

FIG. 7 is a schematic view of a pressurized carbon dioxide bathing apparatus according to Embodiment 5 of the invention.

In this Embodiment, a frame to adjust the pressure is provided outside of the pressurizing layer of the cover suit. In addition, in FIG. 7, parts with the same configurations as in FIG. 1 are assigned the same reference numerals to omit descriptions thereof.

In FIG. 7, a cover suit 60 is formed from an inner cover suit 60A and outer cover suit 60B. The inner cover suit 60A and outer cover suit 60B are formed integrally. Then, a frame 64 for pressure adjustments is provided on the outer surface of the outer cover suit 60B. To the inside of the inner cover suit 60A is supplied the mixed gas of carbon dioxide and water vapor from the carbon dioxide supply apparatus 1, and next, to the inside of the outer cover suit 60B is supplied compressed air from the compressor 2. By this means, a mixed gas layer 61 of carbon dioxide and water vapor is formed between the inner cover suit 60A and skin, and a pressurizing layer 62 comprised of compressed air is formed between the inner cover suit 60A and outer cover suit 60B. The pressurizing layer 62 pressurizes the mixed gas layer 61 of carbon dioxide and water vapor against the skin from the outside to promote absorption of carbon dioxide from the skin.

As shown in FIG. 7, in an opening of the cover suit 60, a fastening portion 63 is provided, fastened to fit the body at a position in accordance with the body shape of a user, and prevents the gas from leaking. Herein, the frame 64 is made of, for example, nylon resin or the like, and is configured to be wound in the shape of a ring or spiral outside the outer cover suit 60B and fixed. Further, for the lower limb as shown in FIG. 7, the radius of the ring or spiral decreases as the distance increases toward the ankle from the femora, for example, and thus, the frame 64 is formed in accordance with the schematic shape of the body. By this means, the pressure of the pressurizing layer 62 is prevented from being applied outward, and since pressurization can be performed uniformly in accordance with the schematic shape of the body, it is possible to further enhance absorption efficiency of carbon dioxide into skin.

In addition, the above-mentioned Embodiments are described using the human body as a target for performing pressured dioxide carbon bathing, but the invention is not limited thereto, and may target animals. An Embodiment of the case targeted for animals will be described below.

Embodiment 6

Figure 8:
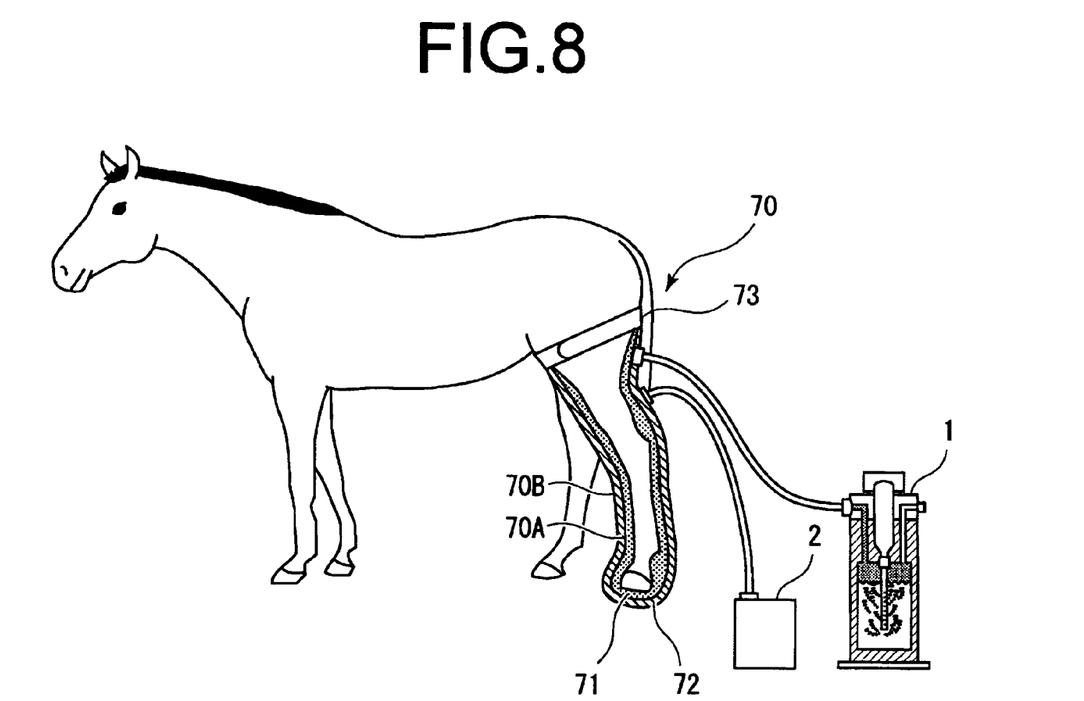
FIG. 8 is a schematic view of a pressurized carbon dioxide bathing apparatus (for horses) according to Embodiment 6 of the invention.

FIG. 8 is a schematic view of a pressurized carbon dioxide bathing apparatus according to Embodiment 6 of the invention. Herein, descriptions are made using a horse as an example of animals targeted for pressurized carbon dioxide bathing. In addition, in FIG. 8, parts with the same configurations as in FIG. 1 are assigned the same reference numerals to omit descriptions thereof.

In FIG. 8, a cover suit 70 is formed from an inner cover suit 70A and outer cover suit 70B. The inner cover suit 70A and outer cover suit 70B are formed integrally, to the inside of the inner cover suit 70A is supplied the mixed gas of carbon dioxide and water vapor from the carbon dioxide supply apparatus 1, and next, to the inside of the outer cover suit 70B is supplied compressed air from the compressor 2. By this means, a mixed gas layer 71 of carbon dioxide and water vapor is formed between the inner cover suit 70A and skin of the horse, and a pressurizing layer 72 comprised of compressed air is formed between the inner cover suit 70A and outer cover suit 70B. The pressurizing layer 72 pressurizes the mixed gas layer 71 of carbon dioxide and water vapor against the skin from the outside to promote absorption of carbon dioxide from the skin of the horse.

As shown in FIG. 8, in this Embodiment, the cover suit 70 has the shape of covering and enveloping the entire hind leg of the horse. In an opening of the thigh region, a fastening portion 73 is provided, fastened to fit the body at a position in accordance with the body shape, and prevents the gas from leaking. The fastening portion is preferably formed of a cord, rubber band or combination thereof, as well as the hook-and-loop fastener. Further, such a structure may be adopted that enables fastening by tightening with air pressure.

Thus, the pressurized carbon dioxide bathing apparatus of the invention is applicable to not only the human body, but also animals (for example, racehorses, pets, etc.).

As described above, the pressurized carbon dioxide bathing apparatus according to the invention has a cover suit of a two-layer structure which has an enclosed layer for confining a mixed gas of carbon dioxide and water vapor supplied from the carbon dioxide supply means to bring the mixed gas of carbon dioxide and water vapor into direct contact with skin of a living body, while having an enclosed layer for confining compressed air supplied from the compressed air supply means, thereby brings carbon dioxide into contact with skin of the living body by a predetermined pressure value or more using the compressed air, and thus remarkably enhances permeability of carbon dioxide from the skin. Further, since it is not necessary to increase the pressure of the mixed gas of carbon dioxide and water vapor itself, a large amount of carbon dioxide is not required, and it is possible to cause carbon dioxide to be efficiently absorbed from the skin. Furthermore, since carbon dioxide is supplied while being contained in water vapor containing one or a plurality of chemical agents, it is possible to further add effects such as blood circulation promotion, sterilization and the like specific to each chemical agent.

In the foregoing, the Embodiments of the invention are described, but the invention is not limited to the above-mentioned Embodiments, and various modifications thereof are capable of being made based on the subject matter of the invention, and should not be excluded from the scope of the invention.

INDUSTRIAL APPLICABILITY

The present invention relates to a pressurized carbon dioxide bathing apparatus for bringing carbon dioxide into direct contact with skin of a living body, thereby enlarging the blood vessel and improving the blood circulation, and more particularly, to a pressurized carbon dioxide bathing apparatus for bringing carbon dioxide into contact with skin of a living body by a predetermined pressure value or more using compressed air, and thereby enhancing absorption efficiency of carbon dioxide from the skin, and has industrial applicability.

The invention claimed is:

1. A pressurized carbon dioxide bathing apparatus which is to bring carbon dioxide with a concentration of a predetermined value or more into contact with skin of a human body, thereby enlarge the blood vessel and improve the blood circulation, comprising:
   a carbon dioxide supply unit to supply carbon dioxide being contained in water vapor containing one or a plurality of chemical agents;
   a compressed air supply unit; and
   a cover suit of a two-layer structure which is connected to the carbon dioxide supply unit and the compressed air supply unit via connectors, and brings a mixed gas of carbon dioxide and the water vapor containing the one or the plurality of chemical agents supplied from the carbon dioxide supply unit into direct contact with skin of the human body, while forming an enclosed layer for confining compressed air supplied from the compressed air supply unit,
   wherein the carbon dioxide supply unit has a carbon dioxide bottle with carbon dioxide, water, a carbon dioxide inserting portion to which the carbon dioxide bottle with carbon dioxide filled therein is inserted, a water-retaining portion for receiving water containing the one or the plurality of chemical agents, and a mixed gas supply opening communicating with one of the connectors of the cover suit, the carbon dioxide inserting portion releasing the carbon dioxide inside the carbon oxide bottle into the water containing the one or the plurality of chemical agents in the water-retaining portion in bubble form of fine-particle size, thereby obtaining the mixed gas of carbon dioxide and water vapor containing the one or the plurality of chemical agents, and
   wherein the mixed gas of carbon dioxide and water vapor containing the one or the plurality of chemical agents from the carbon dioxide supply unit is brought into contact with the skin of the human body with the predetermined pressure value or more by the compressed air.

2. A pressurized carbon dioxide bathing apparatus which is to bring carbon dioxide with a concentration of a predetermined value or more into contact with skin of an animal, thereby enlarge the blood vessel and improve the blood circulation, comprising:
   a carbon dioxide supply unit to supply carbon dioxide being contained in water vapor containing one or a plurality of chemical agents;
   a compressed air supply unit; and
   a cover suit of a two-layer structure which is connected to the carbon dioxide supply unit and the compressed air supply unit via connectors, and brings a mixed gas of carbon dioxide and the water vapor containing one or the plurality of chemical agents supplied from the carbon dioxide supply unit into direct contact with skin of the animal, while forming an enclosed layer for confining compressed air supplied from the compressed air supply unit,
   wherein the carbon dioxide supply unit has a carbon dioxide bottle with carbon dioxide, water, a carbon dioxide inserting portion to which the carbon dioxide bottle with carbon dioxide filled therein is inserted, a water-retaining portion for receiving water containing the one or the plurality of chemical agents, and a mixed gas supply opening communicating with one of the connectors of the cover suit, the carbon dioxide inserting portion releasing the carbon dioxide inside the carbon oxide bottle into the water containing the one or the plurality of chemical agents in the water-retaining portion in bubble form of fine-particle size, thereby obtaining the mixed gas of carbon dioxide and water vapor containing the one or the plurality of chemical agents, and
   wherein the mixed gas of carbon dioxide and water vapor containing the one or the plurality of chemical agents from the carbon dioxide supply unit is brought into contact with the skin of the animal with the predetermined pressure value or more by the compressed air.

3. The pressurized carbon dioxide bathing apparatus according to claim 1, wherein the compressed air supply unit always performs pressurization using the compressed air.

4. The pressurized carbon dioxide bathing apparatus according to claim 1, wherein the compressed air supply unit performs interval pressurization on the compressed air.

5. The pressurized carbon dioxide bathing apparatus according to claim 1, wherein the one or the plurality of chemical agents is either one or some of vitamin E, vitamin C, photocatalyst and apatite and a complex of cyclodextrin.

6. The pressurized carbon dioxide bathing apparatus according to claim 1, wherein a temperature of water inside the carbon dioxide supply unit ranges from 40° to 70° C.

7. The pressurized carbon dioxide bathing apparatus according to claim 1, wherein the compressed air supply unit has a heating unit, and supplies hot air or cool air by ON/OFF of the heating unit.

8. The pressurized carbon dioxide bathing apparatus according to claim 1, wherein a pressure of the air supplied from the compressed air supply unit ranges from 1.2 to 2.5 atmospheres.

9. The pressurized carbon dioxide bathing apparatus according to claim 8, wherein the compressed air supply unit has a compressed air bottle.

10. The pressurized carbon dioxide bathing apparatus according to claim 8, wherein the compressed air supply unit has an electrically driven compressor.

11. The pressurized carbon dioxide bathing apparatus according to claim 8, wherein the compressed air supply unit has a manual bag-shaped air pressure device.

12. The pressurized carbon dioxide bathing apparatus according to claim 1, wherein the cover suit is a cover suit for a lower body to envelop the lumbar part and lower limbs of the human body.

13. The pressurized carbon dioxide bathing apparatus according to claim 1, wherein the cover suit is a cover suit for an upper body including the abdominal part and upper limbs of the human body.

14. The pressurized carbon dioxide bathing apparatus according to claim 1, wherein the cover suit is a cover suit for single lower limb to envelop one leg of the human body.

15. The pressurized carbon dioxide bathing apparatus according to claim 1, wherein the cover suit is a cover suit for single upper limb to envelop one hand of the human body.

16. The pressurized carbon dioxide bathing apparatus according to claim 2, wherein the cover suit is formed from any one or a combination of some of polyethylene, polypropylene, polyvinylidene chloride, polystyrene, polyvinyl acetate, polyvinyl chloride, nylon or polytetrafluoroethylene, and woven fabric or non-woven fabric.

17. The pressurized carbon dioxide bathing apparatus according to claim 16, wherein the cover suit is provided at its opening portion with a fastening portion that is a cord or hook-and-loop fastener, and thereby prevents the mixed gas and the compressed air from dissipating into the atmosphere.

18. The pressurized carbon dioxide bathing apparatus according to claim 1, wherein each of the connectors, which are provided in the cover suit to receive the mixed gas from the carbon dioxide supply unit and the compressed air from the compressed air supply unit, is a screw-type connector or an insert-type connector with a tap formed therein.

19. The pressurized carbon dioxide bathing apparatus according to claim 1, further comprising a frame disposed over an outer surface of the cover suit, the frame having a ring or a spiral shape to prevent pressure of the mixed gas from being applied outwardly.

* * * * *